(12) United States Patent
Kaufman et al.

(10) Patent No.: US 7,022,820 B2
(45) Date of Patent: Apr. 4, 2006

(54) ANTIBODIES TO THE K12 PROTEIN

(75) Inventors: Russel E. Kaufman, Durham, NC (US); Kimberly Slentz-Kesler, Durham, NC (US)

(73) Assignee: Duke University, Durham, NC (US)

( * ) Notice: Subject to any disclaimer, the term of this patent is extended or adjusted under 35 U.S.C. 154(b) by 341 days.

(21) Appl. No.: 10/080,522

(22) Filed: Feb. 25, 2002

(65) Prior Publication Data

US 2003/0096326 A1 May 22, 2003

Related U.S. Application Data

(63) Continuation of application No. 09/539,774, filed on Mar. 31, 2000, now Pat. No. 6,350,615, which is a continuation of application No. 09/210,474, filed on Dec. 14, 1998, now Pat. No. 6,072,034, which is a continuation of application No. 08/755,559, filed on Nov. 22, 1996, now Pat. No. 5,912,142.

(51) Int. Cl.
*C07K 16/00* (2006.01)
*A61K 39/395* (2006.01)

(52) U.S. Cl. ............... 530/387.1; 530/387.3; 530/388.1; 530/388.8; 424/130.1; 424/133.1; 424/139.1; 424/141.1; 424/156.1

(58) Field of Classification Search ............ 530/387.1, 530/387.3, 388.8, 388.85, 388.1; 424/130.1, 424/156.1

See application file for complete search history.

(56) References Cited

U.S. PATENT DOCUMENTS 5,589,358 A 12/1996 Dawson

FOREIGN PATENT DOCUMENTS

| EP | 0 652 232 | 5/1995 |
| WO | WO 92/13970 | 8/1992 |
| WO | WO 94/00601 | 1/1994 |
| WO | WO 94/00603 | 1/1994 |

OTHER PUBLICATIONS

Fundamental Immunology 242 (William E. Paul, M.D. ed., 3d ed. 1993).*
Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987.*
Lin et al Biochemistry USA vol. 14:1559-1563 (1975.*
Lee, "The Accumulation of Three Specific Proteins Related to Glucose-Regulated Proteins In a Temperature-Sensitive Hamster Mutant Cell Line K12", Journal of Cellular Physiology 106:119-125 (1981).
Cole et al, "Cloning and Expression in *Escherichia coli* K-12 of the Genes for Major Outer Membrane Protein OmpA from *Shigella dysenteriae, Enterobacter aerogenes*, and *Serratia marcescens*", Journal of Bacteriology 149(1): 145-150 (1982).
Slentz-Kesler et al, "Identification and Characterization of K12 (SECTM1), a Novel Human Gene That Encodes a Golgi-Associated Protein with Transmembrane and Secreted Isoforms", Genomics 47:327-340 (1998).

* cited by examiner

*Primary Examiner*—Larry R. Helms
*Assistant Examiner*—David J. Blanchard
(74) *Attorney, Agent, or Firm*—Nixon & Vanderhye P.C.

(57) ABSTRACT

The present invention relates, in general, to a cancer-related protein and to a nucleic acid sequence encoding same. In particular, the invention relates to a protein over expressed in certain neoplastic cells, including breast and ovarian cancer cells, to its encoding sequence, and to diagnostic and treatment methodologies based on same.

5 Claims, 8 Drawing Sheets

| | | | | |
|---|---|---|---|---|
| 1 | MQTCPLAFPG | HVSQALGTLL | FLAASLSAQN | EGWDSPICTE | GVVSVSWGEN |
| 51 | TVMSCNISNA | FSHVNIKLRA | HGQESAIFNE | VAPGYFSRDG | WQLQVQGGVA |
| 101 | QLVIKGARDS | HAGLYMWHLV | GHQRNNRQVT | LEVSGAEPQS | APDTG<u>FWPVP</u> |
| 151 | <u>AVVTAVFILL</u> | <u>VALVMFAWYR</u> | CRCSQQRREK | KFFLLEPQMK | VAALRAGAQQ |
| 201 | GLSRASAELW | TPDSEPTPRP | LALVFKPSPL | GALELLSPQP | LFPYAADP* |

Fig.1

K12 promoter (1-195) and cDNA (196-2180) sequence

```
   1  ATTCCTGCTT CCTTTAGCGT GAACGCGGGT GCGGTGCCTC CCGTGAAATA
  51  ATAAATTCAC CGTCACGCTT GTTGTAACG CGGGTGGTTC CCGAAACTTG
 101  GAGGCTTCCC GTAAACCCAG CTCCTTCCTC ATCTGGGAGG TGGGTCCCGC
                                                        ↓
 151  GCGGGTCCGC CGCCTCCTCC CTGGCCCCTC CCTCTCGTGT CTTTCATTTT
 201  CCTGGGGCTC CGGGGCGCGG AGAAGCTGCA TCCCAGAGGA GCGCGTCCAG
 251  GAGCGGACCC GGGAGTGTTT CAAGAGCCAG TGACAAGGAC CAGGGGCCCA
 301  AGTCCCACCA GCCATGCAGA CCTGCCCCCT GGCATTCCCT GGCCACGTTT
 351  CCCAGGCCCT TGGGACCCTC CTGTTTTGG CTGCCTCCTT GAGTGCTCAG
 401  AATGAAGGCT GGGACAGCCC CATCTGCACA GAGGGGGTAG TCTCTGTGTC
 451  TTGGGGCGAG AACACCGTCA TGTCCTGCAA CATCTCCAAC GCCTTCTCCC
 501  ATGTCAACAT CAAGCTGCGT GCCCACGGGC AGGAGAGCGC CATCTTCAAT
 551  GAGGTGGCTC CAGGCTACTT CTCCCGGGAC GGCTGGCAGC TCCAGGTTCA
 601  GGGAGGCGTG GCACAGCTGG TGATCAAAGG CGCCCGGGAC TCCCATGCTG
 651  GGCTGTACAT GTGGCACCTC GTGGGACACC AGAGAAATAA CAGACAAGTC
 701  ACGCTGGAGG TTTCAGGTGC AGAACCCCAG TCCGCCCCTG ACACTGGGTT
 751  CTGGCCTGTG CCAGCGGTGG TCACTGCTGT CTTCATCCTC TTGGTCGCTC
 801  TGGTCATGTT CGCCTGGTAC AGGTGCCGCT GTTCCCAGCA ACGCCGGGAG
 851  AAGAAGTTCT TCCTCCTAGA ACCCCAGATG AAGGTCGCAG CCCTCAGAGC
 901  GGGAGCCCAG CAGGGCCTGA GCAGAGCCTC CGCTGAACTG TGGACCCCAG
 951  ACTCCGAGCC CACCCCAAGG CCGCTGGCAC TGGTGTTCAA ACCCTCACCA
1001  CTTGGAGCCC TGGAGCTGCT GTCCCCCCA ACCCTTGTTT CCATATGCCG
1051  CAGACCCATA GCCGCCTGCA AGGCAGAGAG GACACAGGAG AGCCAGCCCT
1101  GAGTGCCGAC CTTGGGTGGC GGGGCCTGGG TCTCTCGTCC CACCCGGAGG
1151  GCACAGACAC CGGCTTGCTT GGCAGGCTGG GCCTCTGTGT CACCCACTCC
```

Fig.2A

```
1201  TGGGTGCGTG CAGACCCTTC CCCTCCACCC CCCAGGTCTT CCAAGCTCTG
1251  CTTCCTCAGT TTCCAAAATG GAACCACCTC ACCTCCGCAG CACCCGACTT
1301  ACCAGGACGC ATGCCCCTCC CTCTGCCCTC ATCAAACCCA CAGACCCGGA
1351  CTCCCTTTCT GCCACCCCAG GCTGGTCCGG CCCCAGGTGT GGGGTCCGCT
1401  CTCTCCACTC CCAGGGCTCC GCGCCCAAGT GAGGGGGCCC CTGCCGGAGC
1451  CTCAGACACA CTGGAGTTCA GGGCTGGGGG GGCCTTGGCA CATACCTGTC
1501  CCTTGGCTAT GAGCAGGCTT TGGGGGCCCT TCCGCGGCAG CCCCGGGGGC
1551  CGAGGTAGGG TCTGGGGGCT TAGAGGCTGG GATGGCTCCT GGCCCCACCG
1601  CCAGGGGGCA AGCGCAGGCC GGGCTGGGAG GCGGCGGCGG CGGCTCGGGC
1651  TGGGGGGTCA GGTGGACGCT GCCTCCGGGG CTGGTCGCGC ATCCCTCAGT
1701  CCCTCGGCCA CCCGGGGGTC GCTCCCTCGT GCCCACCGCA CCTGCCGAGC
1751  CTCTTTGGAC CCAGATCTGT TCATGCTTTT GTCTTCGTCA CTGCGGCGGG
1801  GCCCTTTGAT GTCTTCATCT GTATGGGGTG GAAAAATCAC CGGGAATCCC
1851  CCTTCAGTTC TTTGAAAAAG TTCATGACT CGAATATCTG AAATGAAGAA
1901  AACAAACCGA CTCACAAACC TCCAAGTAGC TCCAAATGCA ATTTTAAAA
1951  TGAAAACAA AAATCTGAAA GAAACGTCTT TAGTGGCTTT AAGCCCCAAA
2001  ACGTCCCTAA GGCGTCCTCG AGATGAAGAC GGGGGGGAGC CCCAGCCAGG
2051  TGGAGACCCC GCAGGACGCG GCGGCGCCCG GTGACCGAGG CCTCGCACAG
2101  CCGGCCGCCC TGAGGGTCGG GCCGAGCCAG GGTCCAAGAG GGGCGCGTTT
2151  GTGTCTCGGG TTAAAATAAG GTTCCGTCCG
```

Fig.2B

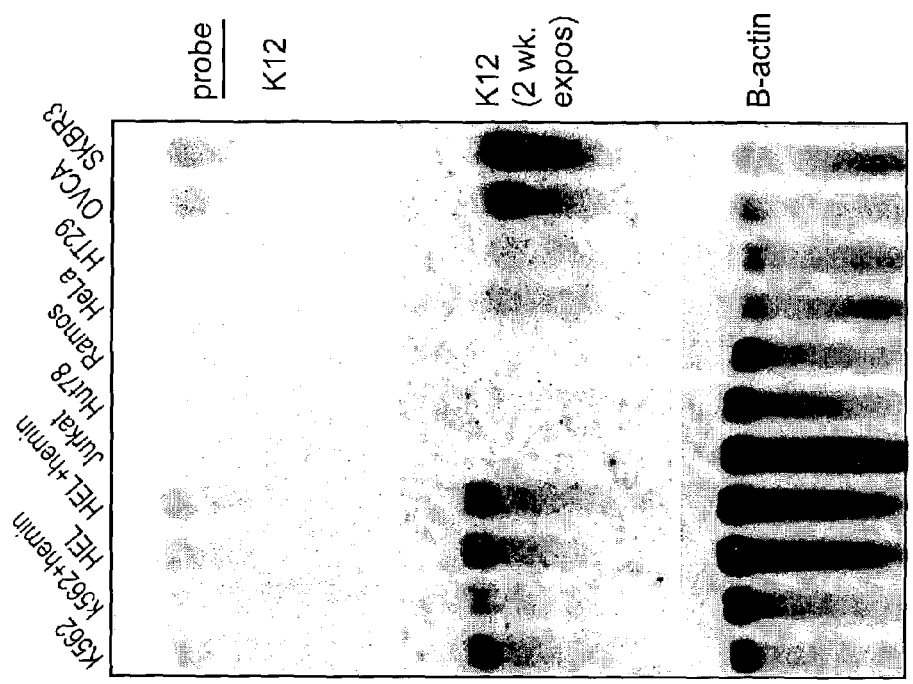
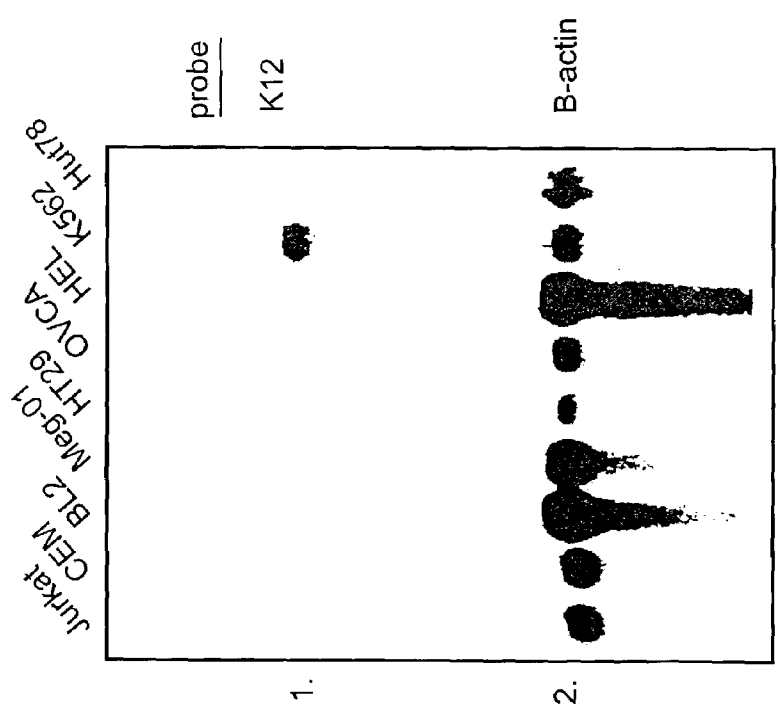
Fig.3B
Fig.3A

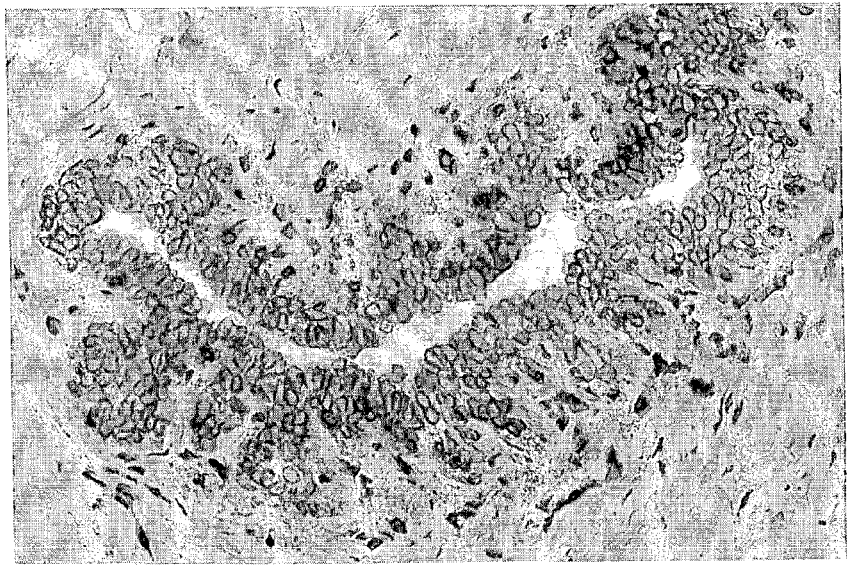
Fig.6A
 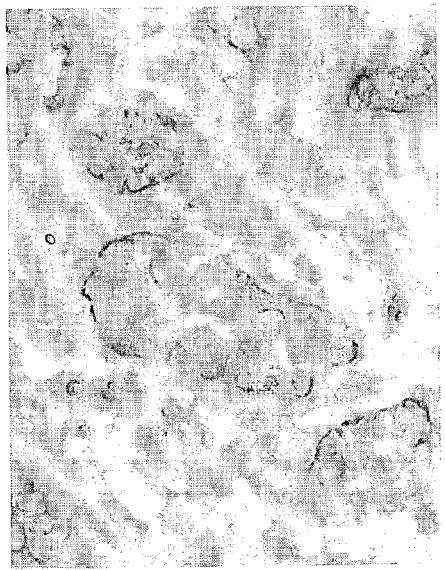
Fig.6B　　　　　　Fig.6C

ANTIBODIES TO THE K12 PROTEIN

This application is a continuation of U.S. application Ser. No. 09/539,774, filed Mar. 31, 2000, now U.S. Pat. No. 6,350,615, which is a continuation of U.S. application Ser. No. 09/210,474, filed Dec. 14, 1998, now U.S. Pat. No. 6,072,034, which is a continuation of U.S. application Ser. No. 08/755,559, filed Nov. 22, 1996, now U.S. Pat. No. 5,912,142. The entire contents of these applications are incorporated herein by reference.

BACKGROUND

Breast cancer represents the most frequent cause of early morbidity and mortality in women in North America (Harris et al, New Eng. J. Med. 327:319, 390 and 473 (1992)). It is generally believed that this malignancy arises from a multi step process involving mutations in a relatively small number of genes, perhaps 10 or less. These mutations result in significant changes in the growth and differentiation of breast tissue that allow it to grow independent of normal cellular controls, to metastasize, and to escape immune surveillance. The genetic heterogeneity of most breast cancers suggests that they arise by a variety of initiating events and that the characteristics of individual cancers are due to the collective pattern of genetic changes that accumulate (Harris et al, New Eng. J. Med. 327:319, 390 and 473 (1992)).

The classes of genes that are involved in breast cancer are not unlike those found in a number of other well characterized malignancies, although some are highly specific for breast cancer. In particular, mutations in the genes that encode receptors involved in binding to estrogen and progesterone are particularly important because they likely cause the breast cells to proliferate while rendering them unresponsive to the antitumor effects of these hormones in advanced malignancy. In addition, changes in the genes that encode growth factors, other receptors, signal transduction molecules, and transcription factor molecules are frequently involved and have alterations that are involved in the development and progression of breast cancer (King, Nature Genetics 2:125 (1992)). The characterization of the type and number of mutations seen in individual breast cancers is useful in classifying the biological properties of individual cancers and in determining the prognosis for individual patients. For example, the erbB2/HER2/neu gene is particularly valuable in predicting the prognosis of both node-positive and node-negative patients based on the amplification status of the gene (King, Science 250:1684 (1990)). Several additional members of this family have been discovered but the ligand for erbB2/HER2/neu remains unknown. It is anticipated that further advances in therapeutics will be achieved by the development of therapies that disrupt aberrant growth signaling pathways or affect the cellular interactions of breast cancer cells with native stroma or metastatic sites.

Although oncogenes are likely to be very important in breast cancer, tumor suppressor genes may also play an important role. Certain of these genes, including p53 and Rb-1, are essential to the normal mechanisms that control cell cycle events, especially those checkpoints at the border of the different stages of the cell cycle (Hollstein et al, Science 253:49 (1991); Srivastava et al, Nature 348:747 (1990)).

In 1969, Li and Fraumeni documented a familial cancer syndrome that had an autosomal dominant pattern of expression (Li et al, Ann. Intern. Med. 71:747 (1969)). Members of these families had sarcomas, breast cancers, brain tumors, leukemias, adrenocortical carcinomas, and other malignancies. Family studies demonstrated that the gene responsible for the syndrome was located on chromosome 17, and examination of the p53 gene as a candidate gene revealed that this gene was mutated in five families (Malsin et al, Science 250:1233 (1990)). In the last two years, two genes linked to familial breast cancer, designated BRCA1 and BRCA2, have been isolated and characterized. BRCA1 is at 17q21 (Claus et al, Am. J. Epidemiology 131:961 (1990); Hall et al, Science 250:1684 (1990); Easton et al, Am. J. of Human Genetics 52(4):678 (1993); Black et al, Am. J. of Human Genetics 52(4):702 (1993); Bowcock et al, Am. J. of Human Genetics 52(4):718 (1993); Miki et al, Science 266:66 (1995)). The demonstration of loss of heterozygosity (LOH) at 17q25 has defined another potential tumor suppressor gene (Lindblom et al, Human Genetics 91:6 (1993); Cornelis et al, Oncogene 8:781 (1993); Theile et al, Oncogene 10:439 (1995)).

The present invention relates at least in part, to a novel gene at 17q25 designated K12. K12 encodes a product that is secreted by cancer cells, for example, breast and ovarian cancer cells. The gene is expressed in these tissues at a level that is at least 100 times higher than that of any other malignant or normal tissue examined. The discovery of the K12 gene makes possible novel tumor detection and treatment methodologies.

OBJECTS AND SUMMARY OF THE INVENTION

It is a general object of the invention to provide a novel cancer-related protein and nucleic acid sequence encoding same.

It is another object of the invention to provide a method of detecting the presence of neoplastic cells, including breast and ovarian cancer cells, in a biological sample.

It is a further object of the invention to provide a method of treating a neoplastic condition in a mammal in need of such treatment.

It is yet another object of the invention to provide a method of screening compounds for their ability to bind to, or alter the activity of, the K12 gene product.

In one embodiment, the present invention relates to an isolated nucleic acid encoding the K12 protein, or portion thereof of at least 15 consecutive bases, or complement thereof. The invention also relates to a recombinant molecule comprising such a nucleic acid and a vector, and to a host cell comprising same. In addition, the present invention relates to a method of producing the K12 protein, or portion thereof of at least 5 amino acids, comprising culturing the above-described host cells under conditions such that the nucleic acid is expressed and the K12 protein, or portion thereof, is thereby produced.

In a further embodiment, the present invention relates to an isolated nucleic acid consisting essentially of a double-stranded DNA molecule, one strand of which encodes the K12 protein, or portion thereof of at least 15 consecutive base pairs. The invention also relates to a recombinant molecule comprising such a nucleic acid operably linked to and in inverse orientation with respect to a promoter. The invention further relates to a method of inhibiting K12 protein production in a host cell comprising introducing into the cell such a recombinant molecule under conditions such that the nucleic acid is transcribed and production of the K12 protein is thereby inhibited.

In yet another embodiment, the present invention relates to a method of screening a test compound for its ability to bind to or otherwise alter the growth stimulatory activity of the K12 protein. The method comprises comparing the K12 protein activity using a culture of cells susceptible to the growth stimulatory effects of the K12 protein, in the presence and absence of the test compound. A reduction in the growth of the cells in the presence of the test compound is indicative of a K12 protein inhibitory activity of the test compound, an increase in the growth of the cells being indicative of a K12 protein activating activity of the test compound.

Further objects and advantages of the present invention will be clear from the description that follows.

BRIEF DESCRIPTION OF THE DRAWINGS

FIG. 1. Predicted amino acid sequence of the human K12 gene product deduced from the human K12 cDNA sequence (SEQ ID NO:1). The underlined region is the proposed membrane spanning domain.

FIG. 2. Human K12 cDNA sequence) (SEQ ID NO:2). K12 promoter (1-195) and cDNA (196-2180).

FIGS. 3A–D. K12 expression.

FIG. 6. Immunoperoxidase staining of normal breast tissue, A, and colloid breast carcinoma, B, with monoclonal antibody 7C3 against K12. C is a isotype matched P3 control. Dark brown staining reflects monoclonal antibody binding to K12 antigen.

DETAILED DESCRIPTION OF THE INVENTION

Figure 3D:
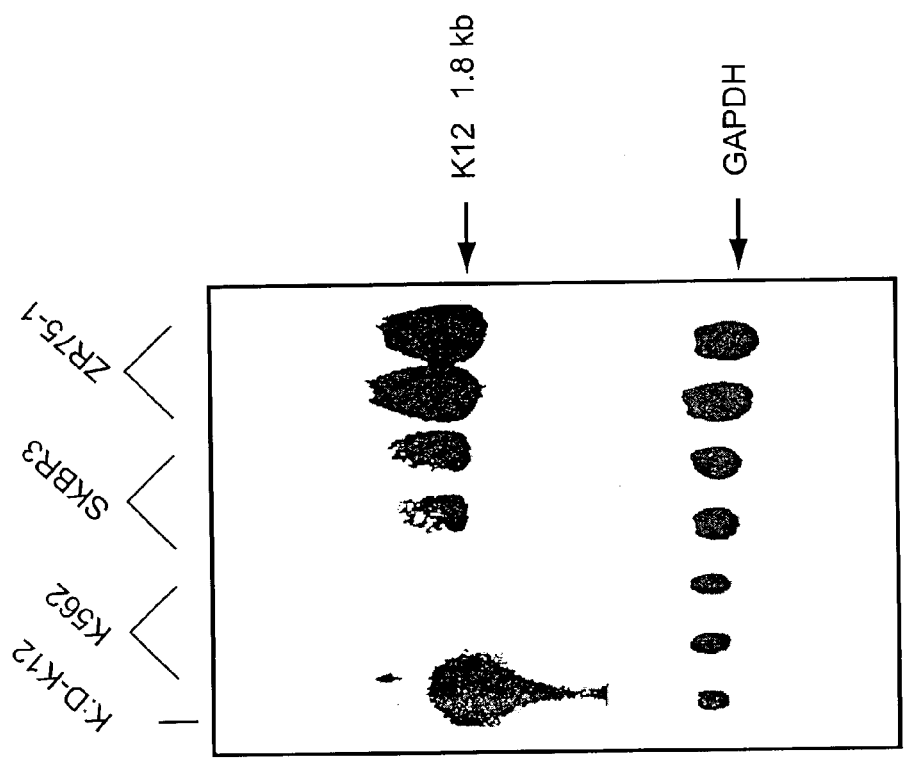

The present invention relates to the mammalian K12 gene product and nucleic acid sequence encoding same. The K12 gene product is over expressed in certain cancer cells, including breast and ovarian cancer cells, and thus provides a useful marker for cancer in cytopathology. As the K12 protein is secreted by certain cancers (including breast and ovarian cancers), its presence in, for example, serum, can be used in detecting the presence of neoplastic cells and/or monitoring tumor progress in a mammal. The identification of K12 as a cancer-related gene makes possible new methods of cancer treatment, in addition to new approaches to tumor detection.

The present invention relates generally to a nucleic acid sequence encoding a K12 protein, particularly, a mammalian K12 protein, more particularly, human K12 protein, or portion of that encoding sequence. The invention further relates to the encoded protein, polypeptide or peptide. The term "portion", as used herein, and as applied to nucleic acid sequences, refers to fragments of at least 15 bases, preferably, at least 30 bases, more preferably, at least 150 bases and, most preferably, at least 300 or 500 bases. As applied to proteins, the term "portion" relates to peptides and polypeptides of at least 5 amino acids, preferably, at least 10 amino acids, more preferably, at least 50 amino acids and most preferably, at least 100 or 240 amino acids. The invention also relates recombinant molecules comprising the above nucleic acid sequences and to host cells tranformed therewith. In addition, the invention relates to methods of making the protein, polypeptide or peptide encoded in the nucleic acid sequence by culturing the transformed host cells under appropriate conditions. Furthermore, the invention relates to methods of screening compounds for the ability to bind to or alter the activity of the K12 gene product. Test compounds can be screened for such abilities, for example, using standard cell culture growth assays and standard binding assays. In addition, the invention relates to cancer detection and treatment methodologies based on the K12 protein and its encoding sequence.

K12 Protein Encoding Sequence Methods of Production and Anti-K12 Antibodies

The present invention relates to nucleotide sequences that encode the amino acid sequence of the mammalian K12 protein, particularly, the human K12 protein, or portions thereof as defined above (eg the extracellular portion, amino acids 1–140). In particular, the present invention relates to nucleotide sequences that encode the amino acid sequence given in FIG. 1, or portions thereof as defined above (the DNA sequence given in FIG. 2 being only an example). Further, nucleotide sequences to which the invention relates include those encoding substantially the same protein as shown in FIG. 1, for example, inter- and intraspecies variations thereof, as well as functional equivalents of the sequence shown in FIG. 1. The invention further relates to nucleotide sequences substantially identical to the sequence shown in FIG. 2. A "substantially identical" sequence is one the complement of which hybridizes to the nucleic acid sequence of FIG. 2 at 55° C. in 3× saline/sodium citrate (SSC) containing 0.1% SDS and which remains bound when subjected to washing at 55° C. with 1×SSC containing 0.1% SDS (note: 20×SSC=3 M sodium chloride/0.3 M sodium citrate). The invention also relates to nucleic acids complementary to those described above.

The present invention also relates to a recombinant molecule comprising a nucleotide sequence as described above and to a host cell transformed therewith. Using standard methodologies, well known in the art, a recombinant molecule comprising a vector and a nucleotide sequence encoding the K12 protein, or portion thereof as defined above, can be constructed. Vectors suitable for use in the present invention include plasmid and viral vectors. Plasmid vectors into which a nucleic sequence encoding the K12 protein, or portion thereof, can be cloned include any vectors compatible with transformation into a selected host cell. Such vectors include SV.NEO and CMV.NEO (eg pcDNA and PC1-neo). The nucleotide sequence of the invention can be present in the vector operably linked to regulatory elements, for example, a promoter. Suitable promoters include, but are not limited to CMV, SV40 and major fat globule protein promoters.

As indicated above, the recombinant molecule of the invention can be constructed so as to be suitable for transforming a host cell. Suitable host cells include prokaryotic cells, such as bacteria, lower eukaryotic cells, such as yeast, and higher eukaryotic cells, such as mammalian cells, and insect cells. The recombinant molecule of the invention can be introduced into appropriate host cells by one skilled in the art using a variety of known methods.

The present invention further relates to a method of producing K12 protein, or portions thereof as defined above. The method comprises culturing the above-described transformed host cells under conditions such that the encoding sequence is expressed and the protein thereby produced.

The nucleic acid sequence(s) of the invention can be used, in accordance with standard protocols, as probes and primers. As such, portions of the K12 gene sequence can be used.

The present invention further relates to the mammalian K12 protein, particularly, the human K12 protein, substantially free of proteins with which it is normally associated, or portions thereof as defined above. The proteins, polypeptides and peptides of the invention can be produced recombinantly using the nucleic acid sequences as described above, or chemically using known methods. The protein of the invention can be produced alone or as a fusion product, for example, with a protein such as betagalactosidase. Such fusion products can be produced recombinantly. For example, the coding sequence of the invention (eg the sequence encoding the mammalian K12 protein) can be cloned in frame with a sequence encoding another protein (such as betagalactosidase) and the fusion product expressed in an appropriate host cell.

The proteins, polypeptides and peptides of the invention can be used as antigens to generate K12 specific antibodies. Methods of antibody generation are well known in the art (see also Example V). Both monoclonal and polyclonal antibodies are included within the scope of the invention, as are binding fragments thereof. The monoclonal antibody 7C3 is preferred. One skilled in the art will appreciate that such antibodies can be used to selectively identify and isolate the K12 protein and portions thereof. In addition, the antibodies can be used in vivo or in vitro to block activity (eg growth stimulatory activity) of the K12 protein.

Compound Screens

The present invention also relates to methods of using the proteins of the invention (eg, recombinantly produced K12 protein) to screen compounds for their ability to bind to or alter (eg inhibit) the activity of K12, and thus to identify compounds that can serve, for example, as K12 protein agonists or antagonists. In a one screening assay, the K12 protein, or portion thereof, is incubated with cells susceptible to the growth stimulatory activity of the K12 protein, in the presence and absence of a compound the K12 activity altering or binding potential of which is to be tested. Growth of the cells is then determined. A reduction in cell growth in the test sample indicates that the test compound binds to and thereby inactivates the K12 protein, or otherwise inhibits the K12 protein activity.

Transgenic animals (e.g. rodents) that over express the K12 gene, for example, in mammary or ovarian tissue, can be used to screen compounds in vivo for the ability to inhibit development of tumors resulting from the K12 over expression or to treat such tumors once developed. Transgenic animals that have mammary tumors of increased invasive or malignant potential can be used to screen compounds, including antibodies or peptides, for their ability to inhibit the effect of K12. Such animals can be produced, for example, as described in Example VIII.

Screening procedures such as those described above are useful for identifying agents for their potential use in pharmacological intervention strategies in such areas as breast or ovarian cancer treatment.

Pharmaceutical Compositions

The present invention also relates to pharmaceutical compositions comprising, as active agent, the proteins, peptides, nucleic acids or antibodies of the invention. The invention also relates to compositions comprising, as active agent, compounds selected using the above-described screening protocols. Such compositions include the active agent in combination with a pharmaceutically acceptable carrier. The amount of active agent in the composition can vary with the agent, the patient and the effect sought. Likewise, the dosing regimen will vary depending on the composition and the disease/disorder to be treated.

Detection/Diagnosis

The present invention further relates to methods of detecting/diagnosing a neoplastic or preneoplastic condition in a mammal (for example, a human). Examples of conditions that can be detected/diagnosed in accordance with these methods include, but are not limited to ovarian tumors, mammary tumors and prostate cancers.

One detection/diagnostic method comprises: (a) obtaining from a mammal (eg a human) a biological sample, (b) detecting the presence in the sample of the K12 protein and (c) comparing the amount of product present with that in a control sample. In accordance with this method, the presence in the sample of elevated levels of the K12 gene product indicates that the subject has a neoplastic or preneoplastic condition.

Biological samples suitable for use in this method include biological fluids such as serum, plasma, pleural effusions, urine and CSF. Since the K12 product is a secreted protein, plasma and/or serum samples are preferred. Tissue samples (eg slices) can also be used in the method of the invention, including samples derived from biopsies. Cell cultures or cell extracts derived, for example, from tissue biopsies can also be used, as can cytospin preparations from pleural effusions.

The detection step of the present method can comprise:

i) contacting the biological sample with a compound (eg a protein) that forms a complex with the K12 gene product under conditions such that the complex can form; and ii) determining the amount of complex formed and comparing that amount with a control sample. (For example, when the biological sample is a pleural effusion, controls can included exudative (eg pneumonia) and non-exudative (eg congestive heart failure) types.)

The compound is preferably a binding protein, eg an antibody, polyclonal or monoclonal, or antigen binding fragment thereof. Monoclonal antibody 7C3 is preferred (a hybridoma producing antibody 7C3 was deposited with the American Type Culture Collection, 12301 Parklawn Drive, Rockville, Md. 20552 (new address: 10801 University Boulevard, Manassas, Va. 20110-2209), on Nov. 19, 1996, under the terms of the Budapest Treaty under Accession No. ATCC HB-12238).

The compound, which can be labeled with a detectable marker (eg fluorophore, chromophore or isotope, etc). Where appropriate, the compound can be attached to a solid support such as a bead, plate, filter, resin, etc.

Determination of formation of the complex can be effected by contacting the complex with a further compound (eg an antibody) that specifically binds to the first compound (or complex). Like the first compound, the further compound can be attached to a solid support and/or can be labeled with a detectable marker.

The identification of elevated levels of K12 protein in accordance with the present invention makes possible the identification of subjects (patients) that are likely to benefit from adjuvant therapy. For example, a biological sample from a post primary therapy subject (eg subject having undergone surgery) can be screened for the presence of circulating K12 protein, the presence of elevated levels of the protein, determined by studies of normal populations, being indicative of residual tumor tissue. Similarly, tissue from the cut site of a surgically removed tumor can be examined (eg immunofluorescently), the presence of elevated levels of product (relative to the surrounding tissue) being indicative of incomplete removal of the tumor. The ability to identify such subjects makes it possible to tailor therapy to the needs of the particular subject. Subjects undergoing non-surgical therapy, eg chemotherapy or radiation therapy, can also be monitored, the presence in samples from such subjects of elevated levels of K12 protein being indicative of the need for continued treatment. Staging of the disease (for example, for purposes of optimizing treatment regimens) can also be effected, for example, by lymph node biopsy eg. with antibody specific for the K12 protein.

The present invention also relates to a kit that can be used in the detection of K12 protein. The kit can comprise a compound that specifically binds the K12 protein (eg binding proteins (eg antibodies or binding fragments thereof (eg F(ab')$_2$ fragments))), for example, disposed within a container means. The kit can further comprise ancillary reagents, including buffers and the like.

The diagnostic methodologies described herein are applicable to both humans and non-human mammals.

Therapy

Antisense oligonucleotides complementary to K12 mRNA can be used to selectively diminish or oblate the expression of the protein. More specifically, antisense contructs or antisense oligonucleotides can be used to inhibit the production of K12 in high expressing cancer (e.g., breast or ovarian) cells. Antisense mRNA can be produced by transfecting into target cancer cells an expression vector with the K12 gene sequence, or portion thereof, oriented in an antisense direction relative to the direction of transcription. Appropriate vectors include viral vectors, including retroviral vectors, as well as nonviral vectors. Tissue specific promoters can be used (eg mammary specific promoters). Alternatively, antisense oligonucleotides can be introduced directly into target cells to achieve the same goal. Oligonucleotides can be selected/designed to achieve the highest level of specificity and, for example, to bind to K12 mRNA at the initiator ATG.

One skilled in the art will appreciate from a reading of this disclosure that monoclonal antibodies to K12 or its receptor can be used to block the action of K12 and thereby control growth of cancer cells. This can be accomplished by infusion of antibodies that bind to K12 and block its action or antibodies to the receptor for K12.

The therapeutic methodologies described herein are applicable to both human and non-human mammals.

Certain aspects of the present invention are described in greater detail in the non-limiting Examples that follow.

EXAMPLE I

Identification and Isolation of K12

A ~500 bp DNA fragment located just upstream of the CD7 HS1 DNase hypersensitive site was used as a probe against an mRNA northern blot and a 1.8 kb transcript was detected in the human erythroleukemic cell line HEL. This 500 bp DNA probe was then used to screen a cDNA library made from the human erythroleukemic cell line K562, and subsequently several clones constituting a 1.8 Kbp cDNA were identified, isolated and designated "K12". The sequence of this cDNA, shown in FIG. 2, reveals a single long open reading frame of 786 bp that is in the same 5' to 3' orientation as CD7. (Schanberg et al, Proc. Natl. Acad. Sci. USA 88:603 (1991).)

EXAMPLE II

Expression Patterns of K12

Figure 3C:
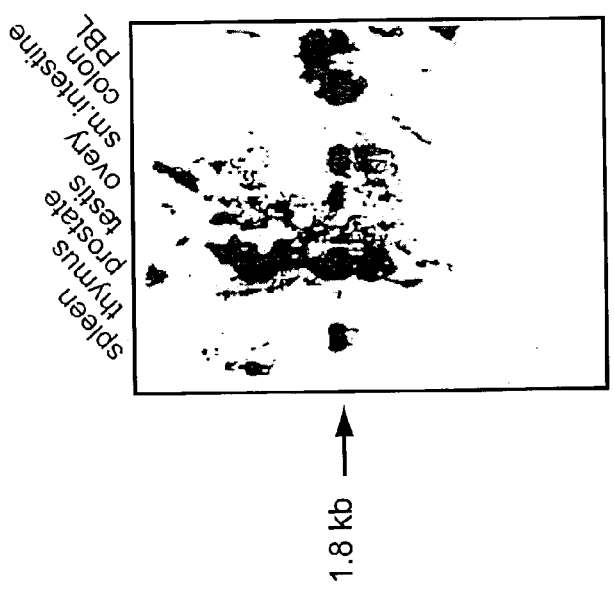

To investigate the range of K12 expression, poly-A+ and total RNAs from many different human cell lines and tissues were analyzed by northern blots probed with radiolabelled K12 cDNA. Northern blots containing 3–4 µg/lane poly-A RNA demonstrate a complete lack of K12 expression in T cell (Jurkat, Hut78, CEM) and B cell (BL2, Ramos) lines, as well as in a megakaryocyte line (Meg-01). A moderately low level of expression was seen in the erythroleukemic cells HEL and K562 (FIG. 3A) and, only after a very long exposure, is K12 mRNA detectable in a colon carcinoma line (HT29) and cervical carcinoma line (HeLa). However, much higher levels are evident in an ovarian cancer (OVCA420) and breast cancer (SKBR3) cell lines (FIG. 3B). A northern blot utilizing 20 µg total RNA/lane for breast cancer lines shows a very high level of K12 RNA accumulation, especially when compared to a lane of poly A+ RNA from K562 cells (FIG. 3D). The first lane contains RNA from K562 cells that are over expressing K12 because it has been transfected with a K12 expression vector. A poly-A+ northern blot (FIG. 3C), demonstrates that K12 is also transcribed in many normal human tissues. This blot shows expression in peripheral blood leukocytes (PBL). The highest level of expression is in granulocytes but expression is seen in monocytes and some lymphocytes by FACS analysis of permeabilized cells with the 7C3 antibody.

EXAMPLE III

Analysis of the Sequence of the Primary Transcript

The cDNA reveals an open reading frame predicting a product of 248 amino acids (FIGS. 1 and 2). This predicts a final unmodified protein of 27 kD, a size that was confirmed by in vitro transcription/translation of K12 RNA. The sequence of the gene is novel and BLAST analysis reveals short regions (10–15 amino acids) of similarity to members of the immunoglobulin supergene family. The predicted primary sequence (FIG. 1) shows two regions of intense hydrophobicity, including a 20 amino acid region near the middle of the molecule, consistent with a membrane spanning domain, and one at the amino terminus, consistent with a leader sequence. The N terminus demonstrates several potential protease cleavage sites as identified near the transmembrane domain.

EXAMPLE IV

Characterization of the Protein Product

Figure 4:
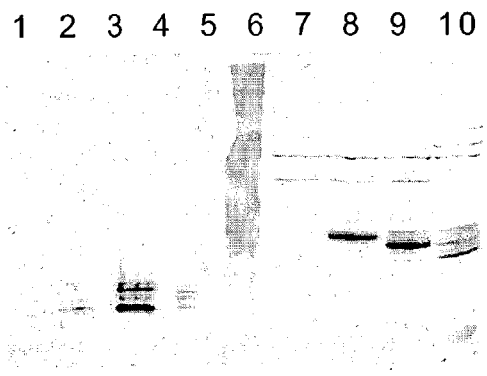
FIG. 4. Western blot probed with antiserum to K12. Concentrated media from K562 cells transfected with: 1) empty vector, 2) K12+7aa flag, 3) K12 with C terminus addition, 4) full length K12, and 5) ZR75-1 cells (not transfected), and 6) molecular weight standards (smallest is 32 kDa). Soluble protein extracts from K562 cells transfected with: 7) empty vector, 8) K12+7aa flag, 9) full length K12, and 10) ZR75-1 cells (not transfected).

A GST-K12 fusion gene was prepared by cloning bases 200–1092 of the K12 cDNA into the cloning site of the PGEX2TK GST fusion vector (Pharmacia). A 55 kDa GST-K12 fusion protein was overexpressed in bacteria, partially purified and injected into rabbits and mice for making both polyclonal and monoclonal antisera. Polyclonal antiserum to K12 was used for western blotting of ZR75-1 protein extracts and a cluster of bands was revealed around 25 kDa, likely indicating cleavage of the signal peptide followed by possible modification of the protein. Many cell lines do not reveal a detectable protein, including K562 which expressed the RNA, but at much lower levels than the breast cancer lines. However K562 cells that were stably transfected to overexpress K12 synthesize a protein product of the same size as seen in breast cancer lines. K562 transfected with the vector alone did not produce K12 detectable with the monoclonal antibody by Western analysis (FIG. 4).

Figure 5A:
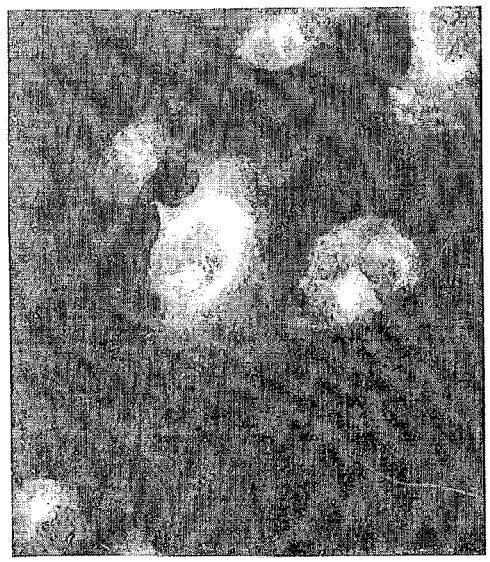
FIG. 5. Subcellular localization of K12 to the Golgi. Same field of view of ZR75-1 cells that were grown on slides, acetone-fixed and double stained with: A, antigen-purified anti-K12 polyclonal antibody followed by FITC-conjugated goat anti-rabbit IgG secondary antibody and B, rhodamine conjugated Wheat Germ Agglutinin (an immunochemical marker for Golgi bodies).
Figure 5B:

In order to determine the localization of K12 within the cell, breast cancer cells were lysed in 100 mM sodium carbonate, pH 11.5. A Western blot of the resulting pellet and supernatant fractions shows that K12 is found in the pellet with other insoluble membrane proteins and further studies show that K12 can be resolubilized in a detergent solution of 1% Triton X-100. These results demonstrate K12 behaves as an integral membrane protein. Immunohistolocalization studies using both fluorescent and light microscopy demonstrated that K12 accumulates in a characteristic perinuclear pattern generally associated with localization to the Golgi bodies (FIG. 5) FACS analysis failed to demonstrate expression on the surface of the cell, whereas it could be detected in permeabilized cells.

EXAMPLE V

Demonstration of Expression of K12 in Breast and Ovarian Cancer Tissues

The anti-K12 monoclonal antibody, 7C3, was produced by fusing spleen cells from a K12 immunized mouse with an immortalized B-cell line. Individual cell hybrids were screened for reactivity to K12 protein and one clone, 7C3, was identified and cloned (Scearce and Eisenbarth, Production of monoclonal activities reacting with the cytoplasm and surface of differentiated cells. Methods in Enzymology, PH Conn (Ed.) vol. 103:459, Academic Press, 1983). The monoclonal antibody was used in immunostaining of acetone fixed normal and malignant breast and ovarian tissues, chosen because of the high level of expression of K12 in breast cancer lines. An isotype matched P3 murine antibody was used as a negative control. All antibodies were conjugated to avidin and the developing system was a biotin horseradish peroxidase. Significant staining occurred only with the 7C3 antibody. Normal glandular elements showed moderate levels of staining with accentuation at the periphery of the glandular tissue (FIG. 6). Stromal tissue demonstrated a low level of general staining typical of molecules in an extracellular location. Breast cancers stained with a higher intensity and islands of malignant cells could be detected. (FIG. 6).

EXAMPLE VI

Demonstration that K12 is a Secreted Molecule

Figure 7:
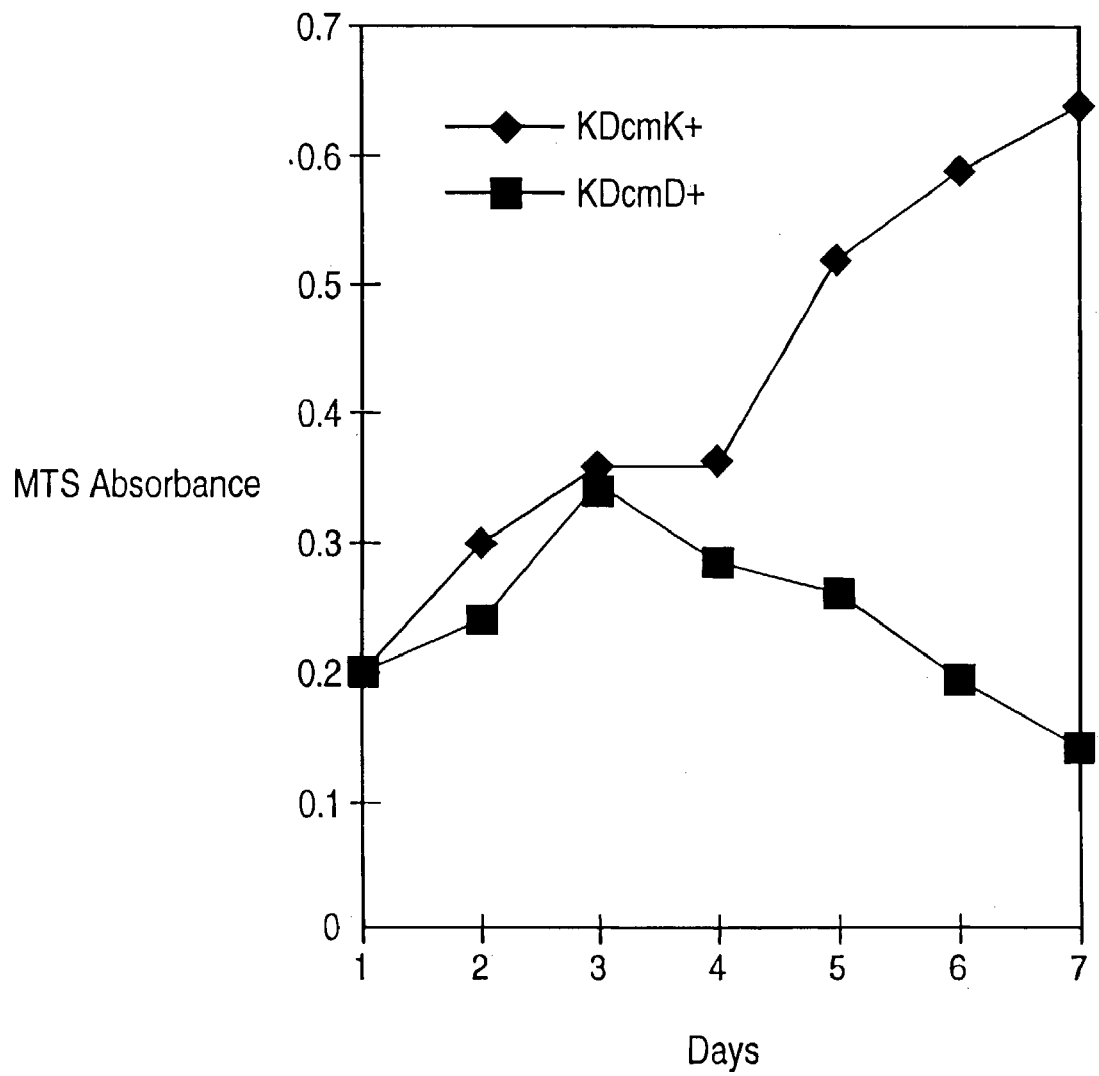
FIG. 7. Growth curves for K562 cells grown in condition media from: KDcmK+(♦), K562 cells secreting K12 into the media, or KdcmD+(■), K562 cells transfected with an empty vector and producing no detectable K12 in media.

Because of the localization to the Golgi, it was hypothesized that the molecule may be secreted. Breast cancer cell lines ZR75-1 and MDAR-MB231 were grown in low serum media, and the supernatant was collected and concentrated. Protein aliquots of concentrated cell supernatants were Western blotted and probed with antigen-purified polyclonal antibodies reactive agents K12. A molecule of approximately 20 kDa was identified, with several bands of lesser intensity but slightly slower mobility, typical of molecules that are glycosylated or modified (FIG. 7).

Although K562 cells express K12 at low levels, no secreted product was identified. However, the normal CMV-K12 cDNA transfected into K562 cells produced K12 product in the media. A K12 gene was produced with an inserted 7 amino acid flag that prevented secretion of the protein, although it could be detected within the cells at high levels. Likewise, cells transfected with empty vector did not secrete K12 in the media. In order to optimize the detection of the secreted product, the transfected cells were grown in media containing reduced amounts of calf serum. Reduction of the serum in the media for all three lines revealed significant reduction in growth rate or survival for all the lines except for those secreting the K12 product. These results indicate a growth regulatory role for the secreted product.

Conditioned media was prepared by growing transfected K562 cells in media supplemented with 0.5% fetal calf serum for two days. Cells transfected with CMV-K12 secreted K12 into their media, whereas cells transfected with empty vector did not. The rate of growth of K562 cells grown in this media was determined (FIG. 7). Only the conditioned media from the cells secreting K12 could sustain the growth of K562 cells in low serum concentration media.

EXAMPLE VII

Expression and Characterization of K12 Receptor

Available data indicate that K12 functions as a growth factor produced by breast glandular tissue and breast cancer cells. Target cells for K12 can be determined by identifying the distribution of receptors of K12 and the binding characteristics. To this end, a K12-immunoglobulin recombinant fusion protein can be prepared (Wee et al, Cell Immunol. 158:353 (1994)) and a determination made as to the cells to which it binds. K562 erythroleukemia cells can be used since these cells were growth responsive to K12 in the conditioned media studies described above and are likely to express a receptor for K12 protein. K562 cells can be incubated with the fusion protein in either PBS or DMEM (with or without 10 mM EDTA) containing 2% BSA and $NaN_3$. After incubation for 30 minutes, the cells can be washed with PBS containing 2% BSA, and fluorescein-conjugated goat anti-human IgG1 can be used as a secondary regent to examine binding in FACS analysis on a FACStar flow cytometer available in the core Flow Cytometry Laboratory at Duke. Specific binding can be determined by the use of human IgG as a control reagent to determine non-specific binding. The ideal binding conditions related to divalent ion concentration and media conditions can be determined and binding characteristics can be determined by Scatchard analysis using a $^{121}$I labeled K12-Ig fusion molecule (Earp et al, Breast Cancer Research & Treatment 35:115 (1995)).

The receptor that binds K12 can be characterized so as to determine whether it is novel or a previously characterized receptor without a known ligand. The cell lines that have the highest level of binding by K12 can be surface labeled with $^{125}$I as described (Aruffo et al, Proc. Natl. Acad. Sci. USA 89:10242 (1992)) then incubated with the K12-Ig fusion protein for 2 hours in DME/5% FBS. After washing with cold PBS, fusion protein can be cross-linked with cell surface proteins with DTSSP or other cross-linker, such as BASED, BS, or SAED. After 60 minute incubation at 4° C., cells can be washed, lysed with NP-40, PMSF and TLCK (Patel et al, J. Exp. Med. 181:1563 (1995)). Ig complexes can then be purified with protein A-Sepharose beads. Solubilized complexes can be examined by SDS gel electrophoresis and by autoradiography. These studies will determine the subunit composition of the receptor. If it is a monomer, the encoding gene can be cloned by either genetic or biochemical methods. If the receptor is composed of different subunits, the subunits can be isolated biochemically and the individual components characterized. If the receptor is novel, the gene encoding it can be cloned by either biochemical purification or expression cloning.

EXAMPLE VIII

Transgenic Animals that Over Express K12

Transgenic mice that overexpress K12 in mammary tissue can be produced as follows. The K12 gene can be linked either to the murine mammary specific promoter for the whey acidic protein (WAP) gene (Leroy et al, Genes, Chromosomes Cancer 6:156 (1993) Sandren et al, Cancer Res. 55:3915 (1995)) or the MMTV promoter (Berard et al, EMBO Journal 13:5570 (1994)) to produce two different transgenic lines (Schanberg et al, J. Immunol. 155:2407 (1995)). An additional mouse line can be produced that utilizes the WAP promoter and a non-secretory variant (non-secretory variants can be produced by the insertion of a 9 amino acid Flag in the amino terminus or leader sequence). The WAP promoter produces high levels of expression in the lactating and pregnant breast of mice and the MMTV promoter produces a broader range of expression in different tissues and very high levels of expression. The MMTV promoter is more likely to produce embryonic or fetal lethals but may permit determination of the effect of over expression of K12 on different tissues during development. Patterns and levels of K12 expression can be determined and the mammary tissues examined on lines of mice during pregnancy and lactation. Mammary tissue can be examined for the presence of atypia or the development of malignancy.

All documents cited above are hereby incorporated in their entirety by reference.

One skilled in the art will appreciate from a reading of this disclosure that various changes in form and detail can be made without departing from the true scope of the invention.

What is claimed is:

1. An isolated antibody, or binding fragment thereof, specific for a protein having the amino acid sequence set forth in SEQ ID NO:1.

2. An isolated antibody, or binding fragment thereof, specific for a protein having at least 240 consecutive amino acids of the amino acid sequence set forth in SEQ ID NO:1.

3. The antibody according to claim 1 wherein said antibody is 7C3 (ATCC Accession No. HB-12238), or binding fragment thereof.

4. The antibody according to claim 1 wherein said antibody is a monoclonal antibody, or binding fragment thereof.

5. A kit comprising the antibody according to claim 1, or binding fragment thereof, disposed within a container means.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 248 amino acids
      (B) TYPE: amino acid
      (C) STRANDEDNESS: <Unknown>
      (D) TOPOLOGY: linear (ii) MOLECULE TYPE: protein (xi) SEQUENCE DESCRIPTION: SEQ ID NO: 1:

```
Met Gln Thr Cys Pro Leu Ala Phe Pro Gly His Val Ser Gln Ala Leu
1               5                   10                  15

Gly Thr Leu Leu Phe Leu Ala Ala Ser Leu Ser Ala Gln Asn Glu Gly
                20                  25                  30

Trp Asp Ser Pro Ile Cys Thr Glu Gly Val Val Ser Val Ser Trp Gly
            35                  40                  45

Glu Asn Thr Val Met Ser Cys Asn Ile Ser Asn Ala Phe Ser His Val
        50                  55                  60

Asn Ile Lys Leu Arg Ala His Gly Gln Glu Ser Ala Ile Phe Asn Glu
65                  70                  75                  80

Val Ala Pro Gly Tyr Phe Ser Arg Asp Gly Trp Gln Leu Gln Val Gln
                85                  90                  95
```

```
Gly Gly Val Ala Gln Leu Val Ile Lys Gly Ala Arg Asp Ser His Ala
            100                 105                 110
Gly Leu Tyr Met Trp His Leu Val Gly His Gln Arg Asn Asn Arg Gln
        115                 120                 125
Val Thr Leu Glu Val Ser Gly Ala Glu Pro Gln Ser Ala Pro Asp Thr
    130                 135                 140
Gly Phe Trp Pro Val Pro Ala Val Val Thr Ala Val Phe Ile Leu Leu
145                 150                 155                 160
Val Ala Leu Val Met Phe Ala Trp Tyr Arg Cys Arg Cys Ser Gln Gln
                165                 170                 175
Arg Arg Glu Lys Lys Phe Phe Leu Leu Glu Pro Gln Met Lys Val Ala
            180                 185                 190
Ala Leu Arg Ala Gly Ala Gln Gln Gly Leu Ser Arg Ala Ser Ala Glu
        195                 200                 205
Leu Trp Thr Pro Asp Ser Glu Pro Thr Pro Arg Pro Leu Ala Leu Val
    210                 215                 220
Phe Lys Pro Ser Pro Leu Gly Ala Leu Glu Leu Leu Ser Pro Gln Pro
225                 230                 235                 240
Leu Phe Pro Tyr Ala Ala Asp Pro
                245
```

(2) INFORMATION FOR SEQ ID NO: 2:

(i) SEQUENCE CHARACTERISTICS:
        (A) LENGTH: 2180 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

```
ATTCCTGCTT CCTTTAGCGT GAACGCGGGT GCGGTGCCTC CCGTGAAATA ATAAATTCAC     60

CGTCACGCTT GTTGTGAACG CGGGTGGTTC CCGAAACTTG GAGGCTTCCC GTAAACCCAG    120

CTCCTTCCTC ATCTGGGAGG TGGGTCCCGC GCGGGTCCGC CGCCTCCTCC CTGGCCCCTC    180

CCTCTCGTGT CTTTCATTTT CCTGGGGCTC CGGGGCGCGG AGAAGCTGCA TCCCAGAGGA    240

GCGCGTCCAG GAGCGGACCC GGGAGTGTTT CAAGAGCCAG TGACAAGGAC CAGGGGCCCA    300

AGTCCCACCA GCCATGCAGA CCTGCCCCCT GGCATTCCCT GGCCACGTTT CCCAGGCCCT    360

TGGGACCCTC CTGTTTTTGG CTGCCTCCTT GAGTGCTCAG AATGAAGGCT GGGACAGCCC    420

CATCTGCACA GAGGGGGTAG TCTCTGTGTC TTGGGGCGAG AACACCGTCA TGTCCTGCAA    480

CATCTCCAAC GCCTTCTCCC ATGTCAACAT CAAGCTGCGT GCCCACGGGC AGGAGAGCGC    540

CATCTTCAAT GAGGTGGCTC CAGGCTACTT CTCCCGGGAC GGCTGGCAGC TCCAGGTTCA    600

GGGAGGCGTG GCACAGCTGG TGATCAAAGG CGCCCGGGAC TCCCATGCTG GCTGTACAT    660

GTGGCACCTC GTGGGACACC AGAGAAATAA CAGACAAGTC ACGCTGGAGG TTTCAGGTGC    720

AGAACCCAG TCCGCCCCTG ACACTGGGTT CTGGCCTGTG CCAGCGGTGG TCACTGCTGT    780

CTTCATCCTC TTGGTCGCTC TGGTCATGTT CGCCTGGTAC AGGTGCCGCT GTTCCCAGCA    840

ACGCCGGGAG AAGAAGTTCT TCCTCCTAGA ACCCCAGATG AAGGTCGCAG CCCTCAGAGC    900

GGGAGCCCAG CAGGGCCTGA GCAGAGCCTC CGCTGAACTG TGGACCCCAG ACTCCGAGCC    960

CACCCCAAGG CCGCTGGCAC TGGTGTTCAA ACCCTCACCA CTTGGAGCCC TGGAGCTGCT   1020

GTCCCCCCCA ACCCTTGTTT CCATATGCCG CAGACCCATA GCCGCCTGCA AGGCAGAGAG   1080
```

```
GACACAGGAG AGCCAGCCCT GAGTGCCGAC CTTGGGTGGC GGGGCCTGGG TCTCTCGTCC    1140

CACCCGGAGG GCACAGACAC CGGCTTGCTT GGCAGGCTGG GCCTCTGTGT CACCCACTCC    1200

TGGGTGCGTG CAGACCCTTC CCCTCCACCC CCCAGGTCTT CCAAGCTCTG CTTCCTCAGT    1260

TTCCAAAATG GAACCACCTC ACCTCCGCAG CACCCGACTT ACCAGGACGC ATGCCCCTCC    1320

CTCTGCCCTC ATCAAACCCA CAGACCCGGA CTCCCTTTCT GCCACCCCAG GCTGGTCCGG    1380

CCCCAGGTGT GGGGTCCGCT CTCTCCACTC CCAGGGCTCC GCGCCCAAGT GAGGGGGCCC    1440

CTGCCGGAGC CTCAGACACA CTGGAGTTCA GGGCTGGGGG GGCCTTGGCA CATACCTGTC    1500

CCTTGGCTAT GAGCAGGCTT TGGGGGCCCT TCCGCGGCAG CCCCGGGGGC CGAGGTAGGG    1560

TCTGGGGGCT TAGAGGCTGG GATGGCTCCT GGCCCCACCG CCAGGGGCA AGCGCAGGCC     1620

GGGCTGGGAG GCGGCGGCGG CGGCTCGGGC TGGGGGGTCA GGTGGACGCT GCCTCCGGGG    1680

CTGGTCGCGC ATCCCTCAGT CCCTCGGCCA CCCGGGGGTC GCTCCCTCGT GCCCACCGCA    1740

CCTGCCGAGC CTCTTTGGAC CCAGATCTGT TCATGCTTTT GTCTTCGTCA CTGCGGCGGG    1800

GCCCTTTGAT GTCTTCATCT GTATGGGGTG GAAAAATCAC CGGGAATCCC CCTTCAGTTC    1860

TTTGAAAAAG TTCCATGACT CGAATATCTG AAATGAAGAA AACAAACCGA CTCACAAACC    1920

TCCAAGTAGC TCCAAATGCA ATTTTTAAAA TGGAAAACAA AAATCTGAAA GAAACGTCTT    1980

TAGTGGCTTT AAGCCCCAAA ACGTCCCTAA GGCGTCCTCG AGATGAAGAC GGGGGGGAGC    2040

CCCAGCCAGG TGGAGACCCC GCAGGACGCG GCGGCGCCCG GTGACCGAGG CCTCGCACAG    2100

CCGGCCGCCC TGAGGGTCGG GCCGAGCCAG GGTCCAAGAG GGGCGCGTTT GTGTCTCGGG    2160

TTAAAATAAG GTTCCGTCCG                                                2180
```